United States Patent [19]
Fan et al.

[11] Patent Number: 5,955,324
[45] Date of Patent: Sep. 21, 1999

[54] PROCESS FOR PRODUCING CARBOHYDRATE OR GLYCOCONJUGATE

[75] Inventors: Jian Qiang Fan, Baltimore; Yuan Chuan Lee, Timonium, both of Md.; Kaoru Takegawa; Shojiro Iwahara, both of Kagawa-ken, Japan; Akihiro Kondo, Akashi, Japan; Ikunoshin Kato, Uji, Japan

[73] Assignee: Takara Shuzo Co., Ltd., Kyoto-Fu, Japan

[21] Appl. No.: 08/914,155

[22] Filed: Aug. 19, 1997

Related U.S. Application Data

[63] Continuation of application No. 08/401,892, Mar. 10, 1995, abandoned.

[30] Foreign Application Priority Data

Mar. 30, 1994 [JP] Japan .................................. 6-082698

[51] Int. Cl.$^6$ ............................ C12P 19/14; C12P 19/26; C08B 37/08
[52] U.S. Cl. ............................... 435/99; 435/72; 435/74; 435/84; 435/96; 435/98; 435/100; 435/101; 536/4.1; 536/17.2; 536/123; 536/123.1
[58] Field of Search .................................. 435/72, 74, 84, 435/96, 98, 100, 101, 99; 536/4.1, 17.2, 123, 123.1

[56] References Cited

U.S. PATENT DOCUMENTS

| | | | |
|---|---|---|---|
| 4,918,009 | 4/1990 | Nilsson ..................................... | 435/73 |
| 5,403,726 | 4/1995 | Wong et al. ............................. | 435/100 |

FOREIGN PATENT DOCUMENTS

| | | |
|---|---|---|
| 5-64594 | 3/1993 | Japan . |
| 5-65108 | 9/1993 | Japan . |

OTHER PUBLICATIONS

Toone et al, Tetrahedron 45(17): 5365–5422, 1989.
Petit et al, Tetrahedron Letters, 32(43):6125–6128 (1991).
Joziasse et al., "α1→3-Galactosytransferase: the use of recombinant enzyme for the synthesis of α-galactosylated glycoconjugates", *Eur. J. Biochem.* 191, pp. 75–83 (1990).

Trimble et al., "Transfer of Glycerol by Endo–β–N–acetylglucosaminidase F to Oligosaccharides during Chitobiose Core Cleavage", *The Journal of Biological Chemistry*, vol. 261, No. 26, pp. 12000–12005, Sep. 15, 1986.

Bardales et al., "Iransgylcoslation and Transfer Reaction Activites of Endo–α–N–acetyl–D–galactosaminidase from *Diplococcus (Streptococcus) pneumoniae*", The Journal of Biological Chemistry, vol. 264, No. 33, pp. 19893–19897, Nov. 25, 1989.

The Japanese Biochemical Society, vol. 65, No. 8, 1993.

Kadowaki et al., "Purification and Characterization of a Novel Fungal Endo–β–N–acetylglucosaminidase Acting on Complex Oligosaccharides of Glycoproteins", Agric. Biol. Chem., 54(1), pp. 97–106, 1990.

Yamamoto et al., "Transglycosylation Activity of *Mucor hiemalis* Endo–β–N–Acetyl–Glucosamindase Moieties Which Transfers Complex Oligosaccharides to the N–Acetylglucosamine Moieties of Peptides", vol. 203, No. 1 Aug. 30, 1994.

*Patent Abstracts of Japan*, vol. 17, No. 376, (C–1084) Jul. 15, 1993.

*Primary Examiner*—Francisco Prats
*Attorney, Agent, or Firm*—Wenderoth, Lind & Ponack, L.L.P.

[57] ABSTRACT

To provide a process for producing a carbohydrate or a glycoconjugate without forming any hydrolytic product of the remodeled sugar chain.

A process for producing a carbohydrate or a glycoconjugate by a remodeling reaction in the presence of a glycosidase which performs the remodeling reaction in an aqueous medium containing a water-soluble ketone and/or dioxane. Examples of the glycosidase include endoglycosidases such as Endo-A. Examples of the ketone include acetone.

2 Claims, 9 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear    (ii) MOLECULE TYPE: peptide    (ix) FEATURE:
      (A) NAME/KEY:
      (B) LOCATION: 4
      (C) IDENTIFICATION METHOD:
      (D) OTHER INFORMATION: note/= "Xaa is a derivative of Asn
         having a sugar residue linked to the amide group of
         the Asn"

(xi) SEQUENCE DESCRIPTION: SEQ ID NO:1:

Gln Val Glu Xaa Lys
1            5

PROCESS FOR PRODUCING CARBOHYDRATE OR GLYCOCONJUGATE

This application is a continuation of now abandoned application Ser. No. 08/401,892 filed Mar. 10, 1995, now abandoned.

BACKGROUND OF THE INVENTION

1. Field of the Invention

This invention relates to a process for producing a remodeled carbohydrate or glycoconjugate by utilizing the transglycosylation activity of a glycosidase.

2. Description of Related Art

Sugar chains of glycoproteins play important roles in various biological phenomenon, such as the immune second-messenger system. Therefore, modification or replacement of sugar chains in glycoproteins is useful for the pharmacological industry.

This technique can create new types of drugs that can be better delivered to the target cells or can have longer activity. Two approaches can be used for this purpose: chemical and enzymatic. Since chemical reactions usually require organic mediums or other harsh conditions, this approach may cause denaturation of glycoproteins. On the other hand, an enzymatic approach is usually carried out in aqueous solutions such as buffer solutions, etc., and thus are not damaging the proteins. Another advantage of an enzymatic method is that it will react more specifically.

The techniques for enzymatically remodeling sugar chains which are generally employed these days involve an exoglycosidase or a glycosyltransferase and sequential conversion starting from the nonreducing end of a sugar chain, as reported by D. H. Joziasse et al., *European Journal of Biochemistry*, 191, 75–83 (1990).

In regard to transglycosylation by an endoglycosidase, R. B. Trimble et al. [*Journal of Biological Chemistry*, 261, 12000–12005 (1986)] have reported one relating to Endo-β-N-acetylglucosaminidase F (Endo-F) from *Flavobacterium meningosepticum* and R. M. Bardales et al. [*Journal of Biological Chemistry*, 264, 19893–19897 (1989)] have reported another one relating to endo-α-N-acetylgalactosaminidase from *Diplococcus pneumoniae*. Glycerol serves as an acceptor in the former report, while glycerol, tris, p-nitrophenol, serine and threonine serve as an acceptor in the latter report.

Reports on a remodeling mechanism, wherein a carbohydrate or a glycoconjugate serves directly as an acceptor, include one relating to Endo-β-N-acetylglucosaminidase A (Endo-A) from *Arthrobacter protophormiae* disclosed by Japanese Patent Laid-Open No. 64594/1993 and one relating to Endo-β-N-acetylglucosaminidase M (Endo-M) from *Mucor hiemalis* described in *Seikagaku*, 65, 1014 (1993).

When a glycoconjugate with a remodeled sugar chain is improved in the stability and biological activities compared with the corresponding natural glycoconjugate, it is highly applicable to drugs, as described above.

However, it is necessary in the conventional remodeling techniques in the presence of exoglycosidases or glycosyltransferases to perform an enzymatic reaction for each sugar residue, which requires a number of reaction steps and highly complicated procedures.

Also, neither a carbohydrate nor a glycoconjugate serves as an acceptor in the above-mentioned transglycosylation with the use of Endo-F or endo-α-N-acetylgalactosaminidase from *Diplococcus pneumoniae*.

On the other hand, the transglycosylation in the presence of Endo-A or Endo-M is a remodeling reaction wherein a carbohydrate or a glycoconjugate serves directly as an acceptor. Thus it is the most convenient and practically useful method for remodeling sugar chains known at the present time.

SUMMARY OF THE INVENTION

Endo-A to be used for remodeling a sugar chain is produced by *Arthrobacter protophormiae* AKU 0647 [This strain was deposited on Aug. 14, 1991 at National Institute of Bioscience and Human-Technology Agency of Industrial Science and Technology (1-3, Higashi 1 chome Tsukuba-shi Ibaraki-ken 305, JAPAN), in accordance with the Budapest Treaty under the accession number FERM BP-4948]. This enzyme digests a sugar chain of the oligomannose type at the site indicated by an arrow in the following Chemical formula 1.

Chemical formula 1

(Man)$_6$GlcNAc—GlcNAc—Asn—(peptide)

This Endo-A participates in a transfer reaction represented by the following Chemical formula 2.

Chemical formula 2

X-GlcNAc-Y+Z→X-GlcNAc-Z+Y

In this transfer reaction, X represent a carbohydrate. When employed as an enzyme, Endo-A acts well on X which is a homooligomer composed of, for example, mannose(Man) or glucose(Glc) or a heterooligomer composed of two or more components selected from among, for example, Man, Glc and N-acetylglucosamine(GlcNAc). When employed as an enzyme, Endo-M acts well on X which is a homooligomer composed of, for example, Man or Glc or a heterooligomer composed of two or more components selected from among, for example, Man, Glc, GlcNAc and galactose(Gal).

Y represent a carbohydrate or a glycoconjugate. Endo-A or Endo-M of the present invention acts well on Y which is a monosaccharide such as Glc, Man or GlcNAc, a homooligomer composed of two or more molecules of a monosaccharide selected therefrom or a heterooligomer composed of two or more components selected therefrom. Also, use can be made of a glycoconjugate having Asn or a polypeptide bound thereto via Asn at the terminal or a glycoconjugate having Thr or Ser or a polypeptide bound thereto via Thr or Ser at the terminal as Y.

Regarding Z which serves as the acceptor in the transfer reaction in the presence of Endo-A or Endo-M, the reaction well proceeds in the presence of a carbohydrate or a glycoconjugate acceptor having a saccharide with free hydroxy group(OH) at the C-4 position at the nonreducing end.

Among acceptor saccharides with free OH at the C-4 position, particularly preferable ones include those which are the same as glucose in the conformation at the C-4 and C-5 positions. Such acceptor saccharides include Glc, glucosamine, GlcNAc, Man, mannosamine, N-acetylmannosamine and allose, and carbohydrates or glycoconjugates having these saccharides at the nonreducing end. Also, Endo-A or Endo-M acts well on α- and β-methylglycosides and α- and β-p-nitrophenylglycosides of carbohydrates, glucose-1-phosphate and mannose-1-phosphate.

The sugar chain transfer reaction with Endo-A or Endo-M is usually started by adding the carbohydrate or glycoconjugate employed as an acceptor to a starting solution containing the starting carbohydrate or glycoconjugate donor the endoglycosidase, buffer salts. This transfer reaction smoothly proceeds when the starting solution is made hydrophobic by adding, for example, an organic medium or an inorganic salt thereto. When methanol is used as the organic medium, for example, the reaction can be used a carbohydrate or a glycoconjugate hardly soluble in water. When Endo-A is used, the reaction well proceeds in the presence of 40% methanol and a relative activity in 50% methanol solution is about 80% in comparison with that in the absence of methanol. Alternatively, DMSO (dimethyl sulfoxide), DMF (N,N-dimethylformamide), etc. may be used.

As described above, the enzymatic remodeling of a sugar chain is highly useful since it can be performed under mild reaction conditions and the specificity of an enzyme can be utilized therein.

In a remodeling reaction of a sugar chain in the presence of an exoglycosidase or endoglycosidase, however, the remodeled sugar chain thus formed is hydrolyzed by glycosidase and thus hydrolytic products which are undesirable for the original purpose are formed.

The purpose of this invention is to provide a process for producing a carbohydrate or a glycoconjugate without forming any hydrolytic product of the remodeled sugar chain.

DETAILED DESCRIPTION OF THE INVENTION

In an aspect, the present invention provides a process for producing a carbohydrate or a glycoconjugate through a remodeling reaction in the presence of a glycosidase characterized by performing the remodeling reaction in an aqueous medium containing water-soluble ketone and/or dioxane.

The present inventors have found that when a reaction for remodeling a carbohydrate or a glycoconjugate in the presence of glycosidase is performed in the presence of a water-soluble organic medium, this reaction efficiently proceeds and the hydrolysis of the remodeled product by the glycosidase is suppressed, and thus the target remodeled product is produced in a high yield. The present invention has been completed based on this finding.

Examples of the glycosidase to be used in the present invention include the exoglycosidase described in *European Journal of Biochemistry* as cited above, while examples of the endoglycosidase to be used herein include the above-mentioned Endo-F, the endo-α-N-acetylgalactosaminidase from *Diplococcus pneumoniae,* Endo-A and Endo-M.

In the presence of a glycosidase selected from among the above-mentioned ones, a transfer reaction represented by the following Chemical formula 3:

Chemical formula 3

(wherein A represent a carbohydrate, B represent a carbohydrate or a glycoconjugate and C represent a carbohydrate or a glycoconjugate) is performed in the present invention. The process of the present invention is performed under such conditions as to suppress the hydrolysis of the product A-C in Chemical formula 3.

These conditions can be achieved by performing the remodeling reaction represented by the above Chemical formula 3 in the presence of a water-soluble organic medium.

A carbohydrate represented by the above Chemical formula 3 as A, for example, is a monosaccharide, a oligomer composed of disaccharide or more, or saccharides having a GlcNAc at terminal thereof. When employed as an enzyme, Endo-A acts well on A which is a homooligomer composed of, for example, Man or Glc or a heterooligomer composed of two or more components selected from among, for example, Man, Glc and GlcNAc, having a GlcNAc at the terminal thereof. When employed as an enzyme, Endo-M acts well on A which is a homooligomer composed of, for example, Man or Glc or a heterooligomer composed of two or more components selected from among, for example, Man, Glc, GlcNAc and Gal, having a GlcNAc at the terminal thereof.

A carbohydrate or a glycoconjugate represented by the above Chemical formula 3 as B or C, for example, is a monosaccharide, a oligomer composed of disaccharide or more. Also, use can be made of a glycoconjugate having amino acid or a polypeptide bound via amino acid at the terminal thereof, or a glycoconjugate having a amino acid or a polypeptide bound via amino acid. Endo-A or Endo-M of the present invention acts well on B or C which is a monosaccharide such as Glc, Man, GlcNAc, Gal, fucose (Fuc), fructose(Fru), xylose(Xyl), p-nitrophenyl glycoside derivate and methylglycoside derivate, a homooligomer composed of two or more molecules of a monosaccharide selected therefrom or a heterooligomer composed of two or more components selected therefrom. Also, use can be made of a glycoconjugate having Asn or a polypeptide bound via Asn at the terminal thereof or a glycoconjugate having Thr or Ser or a polypeptide bound via Thr or Ser at the terminal thereof.

The water-soluble organic medium to be used may be water-soluble ketones and/or dioxane. The remodeling reaction is performed in an aqueous medium containing such medium(s).

Examples of the water-soluble ketones usable herein include acetone, methyl ethyl ketone and diethyl ketone.

The content of the water-soluble ketone and/or dioxane in the aqueous medium, wherein the remodeling reaction is to be performed, is regulated to such a level that the hydrolysis of the remodeled product by a glycosidase can be suppressed and the remodeled product can be obtained efficiently. For example, acetone may be added and employed in 50% (v/v) or less, by taking the stability of the enzyme in the aqueous medium containing acetone and the remodeling reaction efficiency into consideration. Dioxane may be added and employed in 50% (v/v) or less, for the same reason.

The transfer reaction of the present invention is usually carried out by adding a carbohydrate or a glycoconjugate serving as an acceptor to a starting solution containing a starting carbohydrate or glycoconjugate, a glycosidase and a buffer. The starting material or the acceptor may be used in an amount up to saturation without particular restriction. It is preferable that the acceptor is present in excess and therefore the acceptor is usually employed at a concentration of 200 mM or more. In the present invention, however, the reaction would proceed even at an acceptor concentration of about 10 mM. Therefore a remarkable performance is established in a remodeling reaction in the presence of an acceptor which has a poor solubility or can be used only in a limited amount. The amount of the glycosidase to be used in the present invention is not particularly restricted but appropriately selected over a wide range. In usual, it may be 0.1 mU or more, preferably from 3 mU to 10 U, per ml of the starting solution. A buffer suitably used in the present invention is one having a pH value of about 5 to 11. The reaction is usually performed in an acetate buffer of a pH value of about 6.

Now, the present invention will be illustrated in detail by reference to an example wherein Endo-A was used as the glycosidase, $Man_9$-GlcNAc-GlcNAc-Asn (manufactured by Biocarb Chemicals: hereinafter referred to as $M_9GN_2Asn$) and $Man_6$-GlcNAc-GlcNAc-Asn (manufactured by Biocarb Chemicals: hereinafter referred to as $M_6GN_2Asn$) were used as the starting glycoconjugate and GlcNAc (manufactured by Wako Pure Chemical Industries, Ltd.) was used as the acceptor.

TABLE 1

| | |
|---|---|
| Endo-A | 3 mU |
| $M_9GN_2Asn$ | 3 nmol |
| GlcNAc | 10 μmol |
| 25 mM acetate buffer (pH 6.0) (containing 25% medium) | 20 μl |
| reaction temperature | 37° C. |
| reaction time | 10 minute |

The effects of various organic mediums on the remodeling reaction in the presence of Endo-A were studied by using various organic mediums under the reaction conditions as specified in Table 1. Table 2 shows the results. As Table 2 shows, the substrate was cleaved by Endo-A into $Man_9$-GlcNAc (hereinafter referred to simply as $M_9GN$) and GlcNAc-Asn (hereinafter referred to simply as Asn-GN) in the presence of acetone. The $M_9GN$ was transferred to GlcNAc of the acceptor and thus a remodeled sugar chain $Man_9$-GlcNAc-GlcNAc (hereinafter referred to simply as $M_9GN_2$) was formed in a yield of 100%. Accordingly, acetone is superior as an organic medium for the remodeling reaction to previously known ones such as DMF and DMSO. In Table 2, THF represent tetrahydrofuran.

TABLE 2

| mediums | $M_9GN_2$ (%) |
|---|---|
| Water | 37 |
| DMF | 53 |
| DMSO | 70 |
| Acetone | 100 |

TABLE 2-continued

| mediums | $M_9GN_2$ (%) |
|---|---|
| $CH_3CN$ | 9 |
| THF | 13 |

Figure 1:
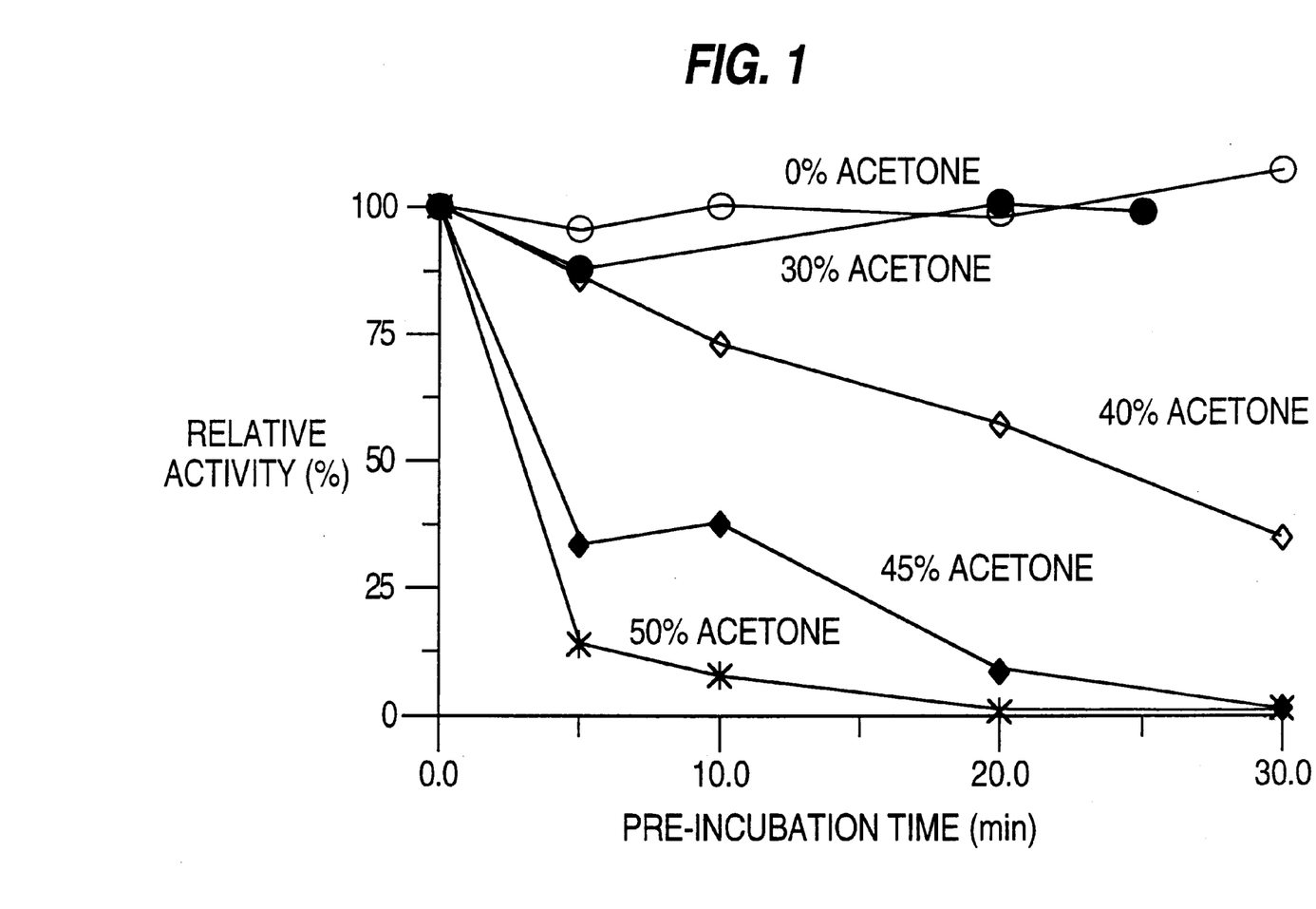
FIG. 1 shows the stability of the enzyme in the presence of acetone at various concentrations.

Next, FIG. 1 shows the stability of Endo-A in aqueous mediums containing acetone. Namely, FIG. 1 shows the results obtained by preincubating 3 mU Endo-A at 37° C. for a given period of time in 20 μl of a 25 mM acetate buffer (pH 6.0) containing acetone at each concentration, adding 1 μl of the preincubated solution to 20 μl of a 25 mM acetate buffer solution containing 3 nmol $M_9GN_2Asn$, performing the reaction at 37° C. for 10 minutes and then determining the activity of Endo-A. The ordinate refers to the relative activity (%) of each treated enzyme determined by taking the activity of the unreacted Endo-A as 100%, while the abscissa refers to the preincubation time (minutes). As FIG. 1 shows, Endo-A was highly stable in an aqueous medium containing 30% acetone.

Figure 2:
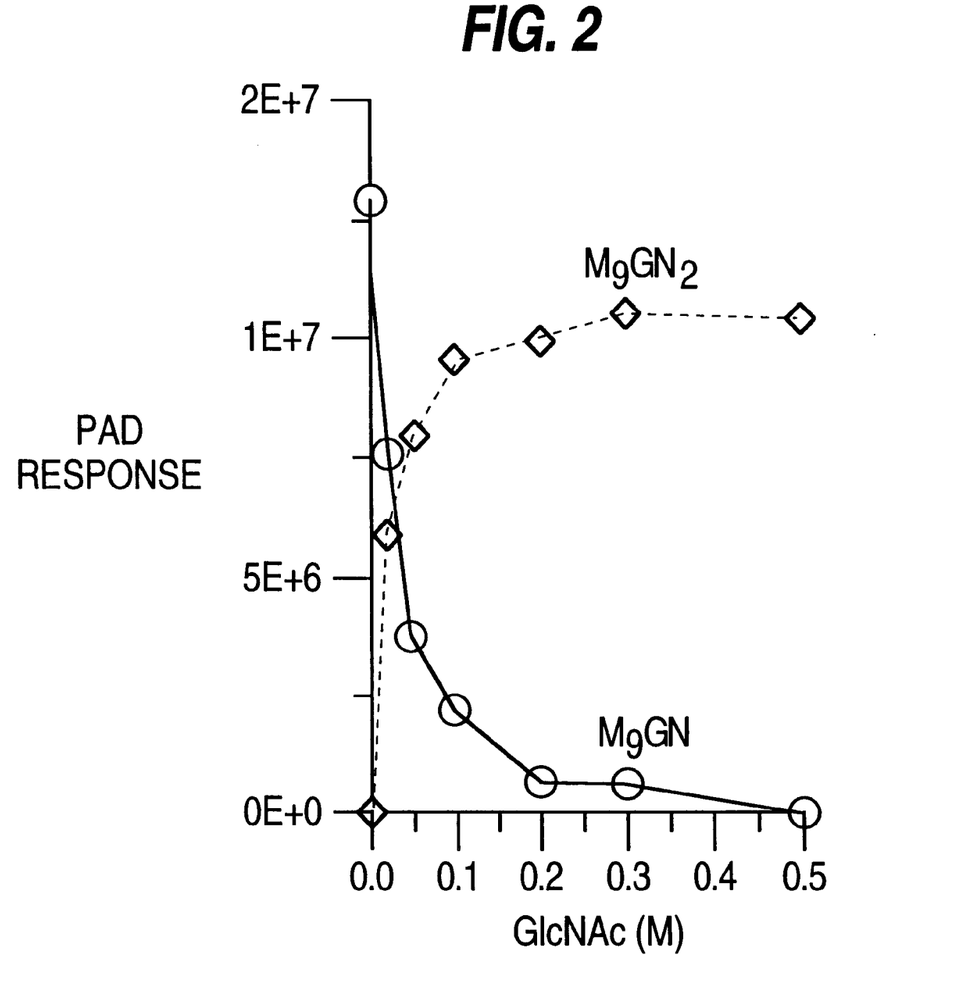
FIG. 2 shows the relation between the donor concentration and the yield of the reaction product.

It is preferable that an acceptor be present in excess in a reaction for remodeling a sugar chain. Next, FIG. 2 shows a relationship between the remodeling reaction and the acceptor concentration in the present invention. Namely, FIG. 2 shows the results obtained by performing the reaction under the conditions in accordance with those specified in Table 1 with the use of GlcNAc at various concentrations in the presence of 30% acetone and determining the amounts of $M_9GN_2$ and $M_9GN$ thus formed by the high performance anion exchange chromatography/pulsed amperomatric detector(HPAEC/PAD) system (manufactured by Dionex Corp.). The ordinate refers to the PAD response, while the abscissa refers to the GlcNAc concentration (M). As FIG. 2 shows, $M_9GN_2$ was sufficiently formed even at 25 mM GlcNAc in the presence of 30% acetone. At 200 mM or above GlcNAc, further, the hydrolysis of the remodeled sugar chain was sufficiently suppressed. At 500 mM GlcNAc, the formation of $M_9GN$ (i.e., the hydrolytic product) was completely suppressed.

Figure 3:
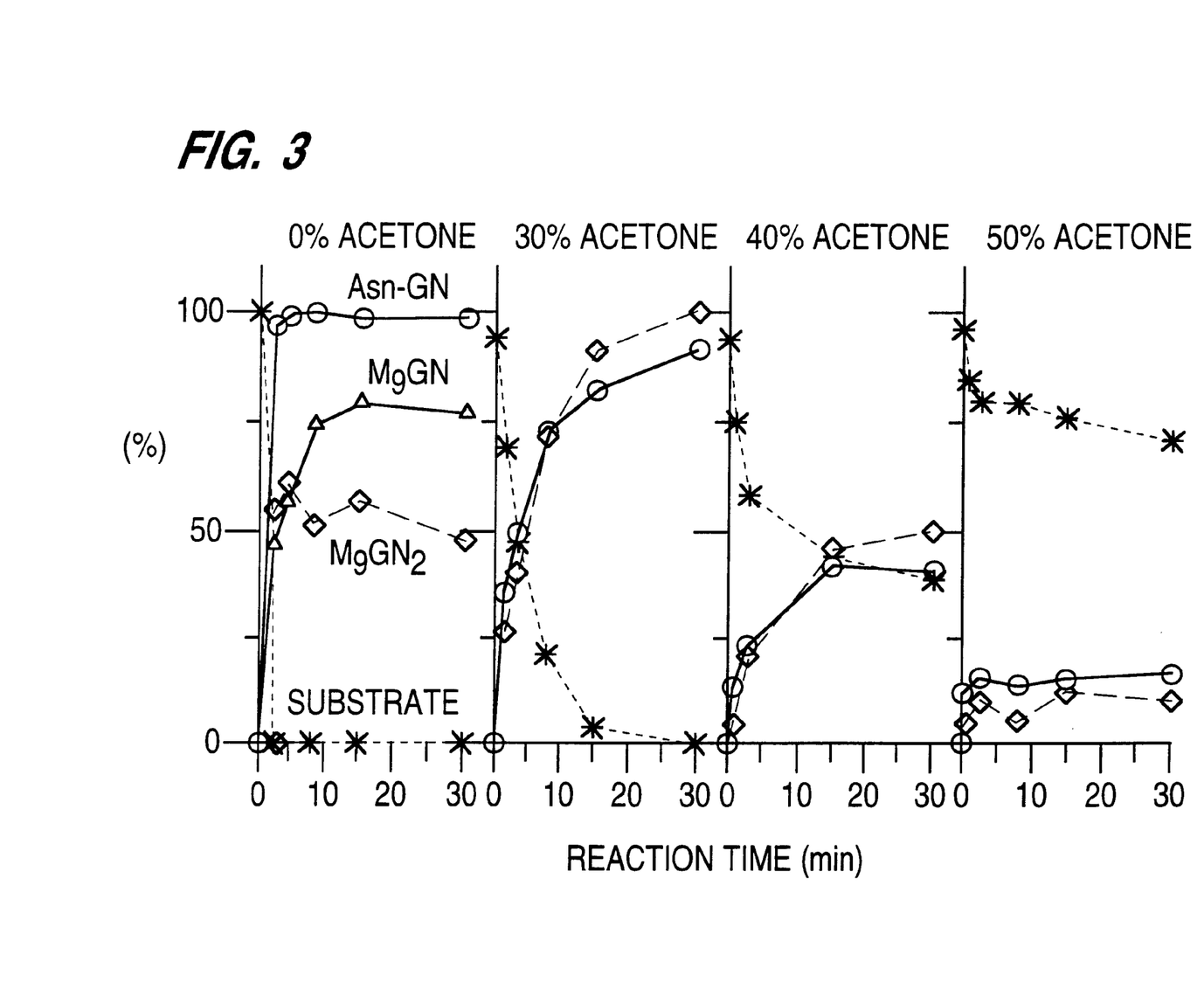
FIG. 3 shows the relation between the yield of the reaction product and time in the presence of acetone at various concentrations.

FIG. 3 shows the formation of the remodeled sugar chain by Endo-A in aqueous mediums containing acetone and an aqueous medium being free therefrom. Namely, FIG. 3 shows the results obtained by performing the reaction under the conditions in accordance with the those specified in Table 1 in the presence of 0, 30, 40 and 50% acetone and determining $M_9GN_2Asn$, $M_9GN_2$, $M_9GN$ and Asn-GN with the passage of time. The ordinate refers to the amount (%) of each substance, while the abscissa refers to the reaction time (minutes). As FIG. 3 shows, no $M_9GN$ was formed in the presence of 30 to 50% acetone. The yield of $M_9GN_2$ in the absence of acetone was about 50%. In contrast, the yield of $M_9GN_2$ in the presence of 30% acetone was 100%.

To discuss acceptors in reaction mixtures containing acetone, furthermore, 20 μl of a 25 mM acetate buffer solution (pH 6.0) each containing 3 nmol of $M_9GN_2Asn$, 4 μmol of an acceptor and 1 mU Endo-A were allowed to react at 37° C. for 15 minutes (in the cases of L-Fuc and L-Gal) or 10 minutes (in the cases of other acceptors) in the presence of 35% (in the cases of L-Fuc and L-Gal) or 30% (in the cases of other acceptors) acetone and the yields (%) of remodeled sugar chains thus formed were determined. Table 3 shows the results. As Table 3 shows, Man, L-Fuc, L-Gal, Fru, Xyl, 2-deoxy-Glc (manufactured by SIGMA), 6-deoxy-Glc (manufactured by SIGMA), methyl-α-GlcNAc (manufactured by SIGMA) and 3-O-Me-Glc (manufactured by SIGMA) underwent transglycosylation.

TABLE 3

| Acceptor | Yields of remodeled sugar chains (%) |
|---|---|
| GlcNAc | 96.5 |
| Man | 86.7 |
| L-Fuc | 25.6 |
| L-Gal | 19.3 |
| Fru | 6.3 |
| Xyl | 24.2 |
| 2-deoxy-Glc | 90.9 |
| 3-deoxy-Glc | 0.0 |
| 6-deoxy-Glc | 77.3 |
| methyl-α-GlcNAc | 94.3 |
| 3-O-Me-Glc | 36.1 |

Figure 4:
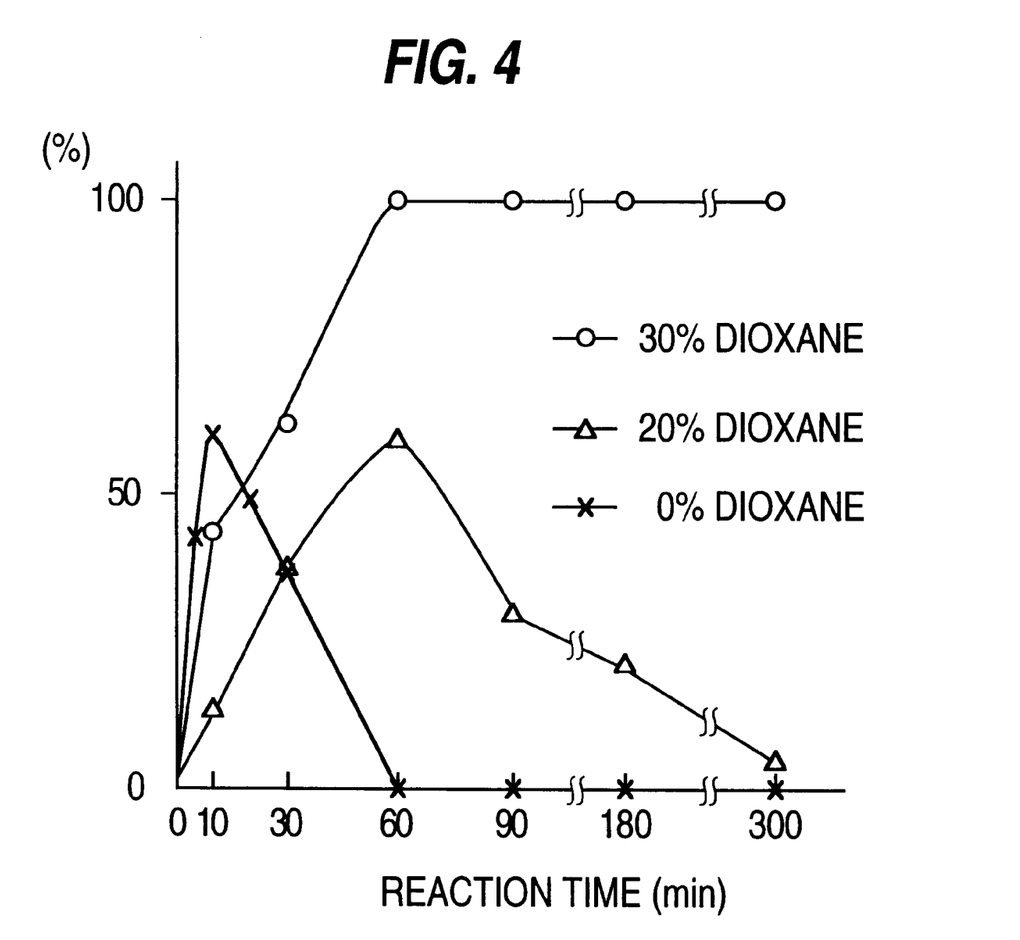
FIG. 4 shows the relation between the yield of a remodeled product and time in the presence of dioxane at various concentrations.

Next, FIG. 4 shows the formation of the remodeled sugar chain by Endo-A in aqueous mediums containing dioxane and an aqueous medium being free therefrom. Namely, FIG. 4 shows the results obtained by monitoring the remodeling reaction in the presence of 0, 20 and 30% dioxane with the passage of time. The ordinate refers to the yield (%) of the remodeled sugar chain, while the abscissa refers to the reaction time (minutes). As FIG. 4 shows, the remodeling reaction efficiently proceeded and the hydrolysis of the remodeled sugar chain was suppressed in the presence of 30% dioxane.

Figure 5:
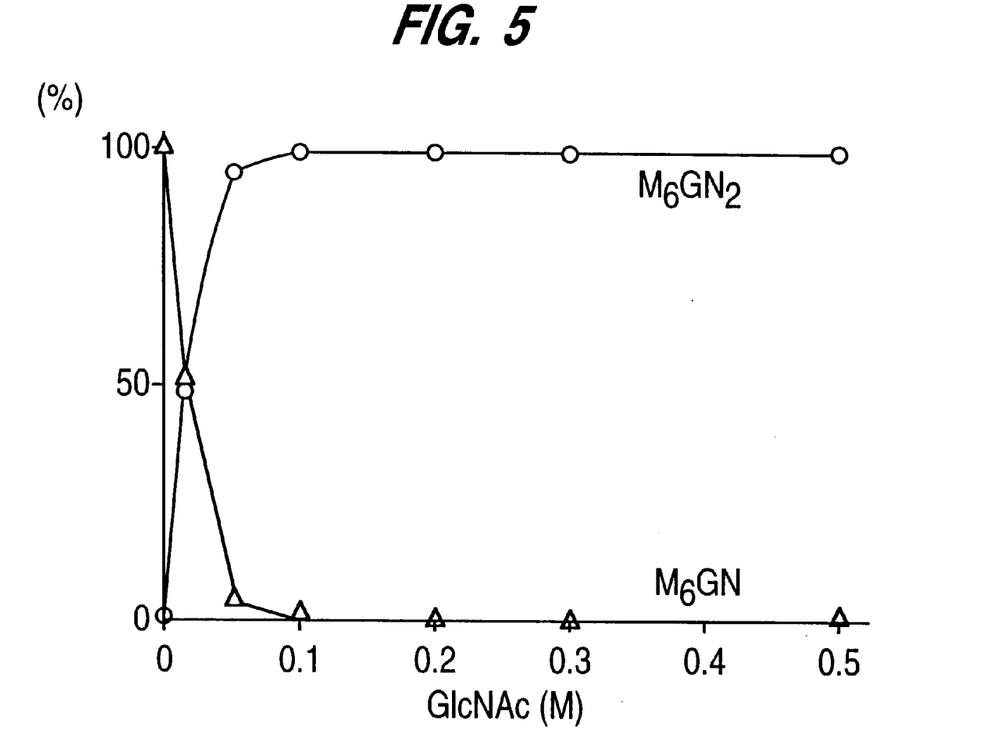
FIG. 5 shows the relation between the donor concentration and the yield of a remodeled product.

FIG. 5 shows a relationship between the acceptor concentration and the remodeled sugar chain thus formed. The ordinate refers to the yield (%) of the remodeled sugar chain, while the abscissa refers to the acceptor concentration (M). As FIG. 5 shows, the remodeling reaction proceeded even at an acceptor concentration of 10 mM and the remodeled sugar chain was formed in a yield of about 50%. At an acceptor concentration of 100 mM or above, further, the yield of the remodeled sugar chain amounted to 100% and the hydrolysis of the remodeled sugar chain was completely suppressed.

As described above, the remodeling efficiency in the transfer reaction of a carbohydrate with a glycosidase can be significantly elevated by adding a specific water soluble organic medium, acetone or dioxane to the reaction mixture.

Either of the above-mentioned acetone and dioxane may be used alone. Alternatively, a combination of acetone with dioxane may be employed.

In the presence of acetone and/or dioxane, the remodeling reaction is performed usually at a temperature from room temperature to about 60° C., preferably from 30 to 40° C., at a pH value of about 5 to 11. The transfer reaction is usually completed within from 5 minutes to 5 hours, preferably from 10 to 60 minutes, though the reaction time varies depending on the reaction conditions.

The remodeled carbohydrate or glycoconjugate thus formed is free from any by-products. Thus it can be easily separated and purified from the reaction mixture in accordance with a publicly known means. For example, the remodeled carbohydrate or glycoconjugate is separated from the reaction mixture by, e.g., gel filtration column chromatography or ion exchange resin column chromatography followed by concentration, desalting, freeze-drying, etc.

According to the present invention, the remodeling reaction proceeds even at a low acceptor concentration and the remodeled product can be efficiently obtained even by an acceptor which has a poor solubility or an acceptor with limited amount. Further, acetone and dioxane make it possible to advance the remodeling at a high reaction rate, compared with DMSO and DMF. Also they have low boiling points and thus can be easily distilled off from the reaction mixture. Therefore they are highly useful as an accelerator for the remodeling reaction.

EXAMPLE 1

Examination of Organic Medium to be Added in Sugar Chain Transfer Reaction with Endo-A To a 25 mM acetate buffer (pH 6.0) were added organic mediums (DMF, DMSO, acetone, $CH_3CN$ and THF), $M_9GN_2Asn$ and GlcNAc in such a manner as to respectively give concentrations of 25%, 3 nmol and 500 mM, thus preparing reaction mixtures. To each reaction mixture was added 3 mU Endo-A (total volume: 20 μl) and incubated at 37° C. for 10 minutes. Then the reaction mixture was evaporated to dryness in vacuo. This dried product was dissolved in water and analyzed by HPAEC/PAD system. Table 2 shows the results.

As Table 2 shows, the yield of $M_9GN_2$ amounted to 100% in the acetone containing reaction mixture.

EXAMPLE 2

Examination of the Stability of Endo-A in Reaction Mixtures Containing Acetone at Various Concentrations To a 25 mM acetate buffer (pH 6.0) was added acetone to give concentrations of 0, 30, 40, 45 and 50%, thus preparing reaction mixtures. To these reaction mixtures was added 3 mU Endo-A (total volume: each 20 μl) and preincubated at 37° C. for 0, 5, 10, 20 and 30 minutes. A 2 μl of each reaction mixture was sampled and added to a 25 mM acetate buffer (pH 6.0) containing 3 nmol of $M_9GN_2Asn$ (which had been separately prepared) and incubated at 37° C. for 10 minutes. After heating at 100° C. for 3 minutes, one-fourth of the reaction mixture was analyzed by the HPAEC/PAD system to thereby examine the remaining enzyme activity. FIG. 1 shows the relationship between the preincubation time (minutes; abscissa) in the acetone containing reaction mixture and the relative activity (%; ordinate). As FIG. 1 shows, the enzyme was hardly inactivated in the presence of 30% acetone.

EXAMPLE 3

Examination of Acceptor Concentration in Sugar Chain Transfer Reaction with Endo-A By using 3 nmol $M_9GN_2Asn$ as the donor, the sugar chain transfer reaction with 3 mU Endo-A was performed in a 25 mM acetate buffer (pH 6.0) containing 30% acetone at 37° C. for 10 minutes while varying the concentration(M) of GlcNAc employed as the acceptor (25, 50, 100, 200, 300 and 500 mM). The reaction was terminated by heating at 100° C. for 3 minutes and $M_9GN$ (i.e., the hydrolytic product) and $M_9GN_2$ (i.e., the remodeled product) were determined by HPAEC/PAD system. FIG. 2 shows the results. In FIG. 2, the ordinate refers to the PAD response, while the abscissa refers to the concentration (M) of GlcNAc. FIG. 2 shows that the transfer reaction almost completely prevailed over the hydrolysis at a GlcNAc concentration of 200 mM or above.

EXAMPLE 4

Change in Sugar Chain Transfer Reaction Product with the Passage of Time 3 nmol of $M_9GN_2Asn$, 50 mM GlcNAc and 3 mU Endo-A were incubated in 20 μl of a 25 mM acetate buffer (pH 6.0) in the presence of O to 50% acetone at 37° C. for 2, 4, 8, 15 and 30 minutes thereafter, the reaction mixture was sampled and analyzed by HPAEC/PAD system. FIG. 3 shows the results. In FIG. 3, the ordinate refers to the yield (%) of the remodeled sugar chain, while the abscissa refers to the reaction time (minutes). As FIG. 3 shows, the sugar chain donor ($M_9GN_2Asn$; *) decreased but the remodeled product $M_9GN_2$ (◇) increased with the passage of time. In the presence of 30% acetone, the remodeled product was obtained in a yield of 100% after 30 minutes.

EXAMPLE 5
Examination of Sugar Chain Transfer Reaction to Various Acceptors in Reaction Mixtures Containing Acetone 20 μl of a 25 mM acetate buffer (pH 6.0) solution each containing 3 nmol $M_9GN_2$Asn as the donor, 4 μmol of an acceptor, 1 mU Endo-A and 35% (in the cases of L-Fuc and L-Gal) or 30% (in the cases of other acceptors) acetone were incubated at 37° C. for 15 minutes (in the cases of L-Fuc and L-Gal) or 10 minutes (in the cases of other acceptors). After terminating the reaction by heating at 100° C. for 3 minutes, each reaction mixture was evaporated to dryness in vacuo. This dried product was dissolved in water ¼ times as much as the reaction mixture and then analyzed by HPAEC/PAD system. Table 3 shows the results. When 2-deoxy-Glc or 3-O-Me-Glc was used as the acceptor, the reaction mixture was analyzed by the high performance liquid chromatogram (HPLC) with a graphitized carbon column (manufactured by Shandon Scientific). Table 3 shows the yields (%) of remodeled sugar chains thus formed by using GlcNAc, Man, L-Fuc, L-Gal, Fru, Xyl, 2-deoxy-Glc, 3-deoxy-Glc, 6-deoxy-Glc, methyl-α-GlcNAc and 3-O-Me-Glc as the acceptor. As Table 3 shows, Man, L-Fuc, L-Gal, Fru, Xyl, 2-deoxy-Glc, 6-deoxy-Glc, methyl α-GlcNAc and 3-0-Me-Glc also underwent transglycosylation.

EXAMPLE 6
Examination of Acetone Concentration in Sugar Chain Transfer Reaction with Endo-A

Figure 6:
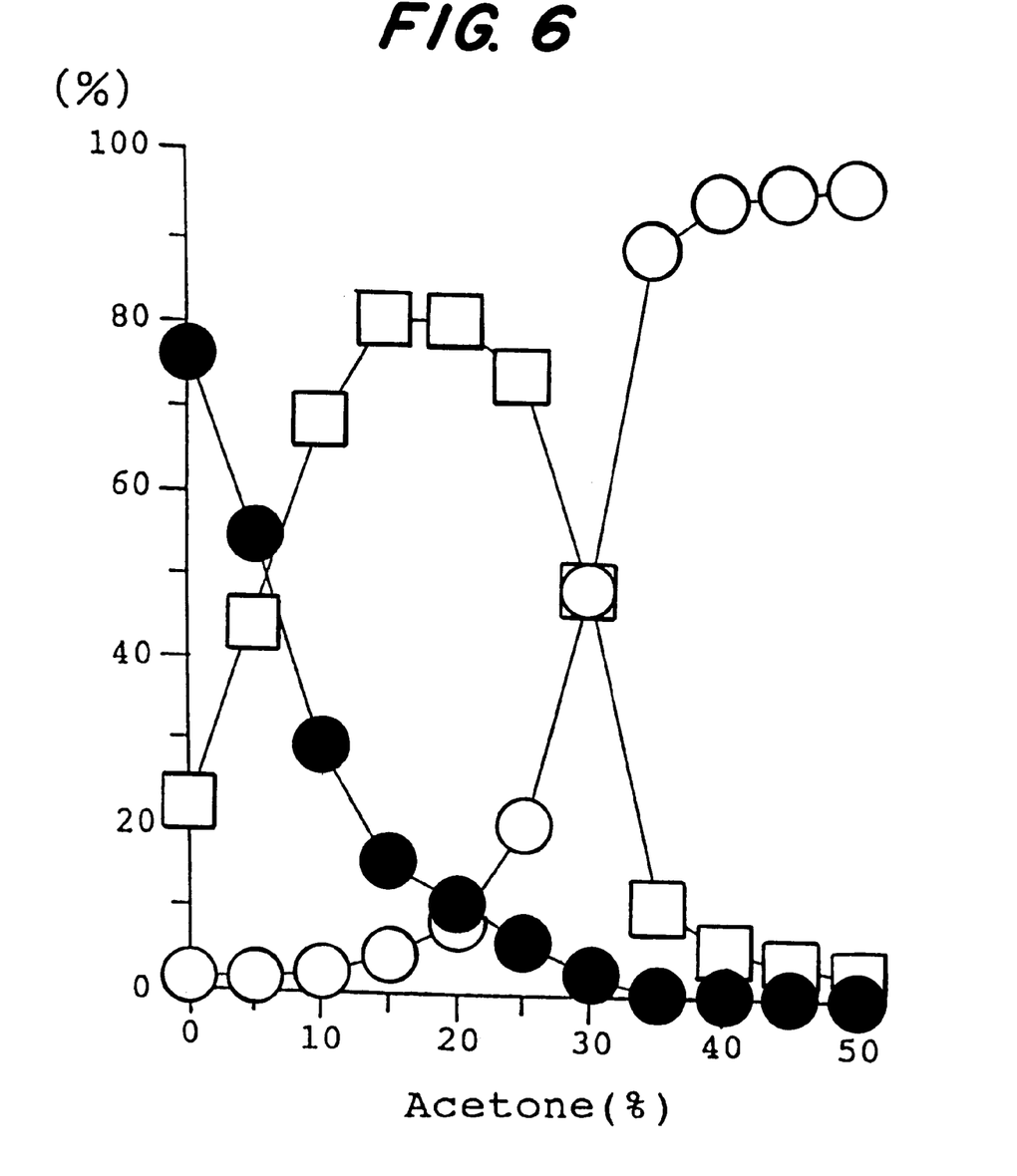
FIG. 6 shows the relations among the acetone concentration and the amounts of the donor, the hydrolytic product and the remodeled product.

20 μl of a 25 mM acetate buffer (pH 6.0) solution containing 3 nmol $M_9GN_2$Asn as the donor, 4 μmol GlcNAc as the acceptor, 1 mU Endo-A and acetone was incubated at 37° C. for 15 minutes. After terminating the reaction by heating at 100° C. for 3 minutes, the reaction mixture was evaporated to dryness in vacuum. This dried product was dissolved in water ¼ times as much as the reaction mixture and then analyzed by HPAEC/PAD system. FIG. 6 shows the results. Namely, FIG. 6 shows the relationships among the acetone concentration (%, abscissa) and the amounts (%, ordinate) of the donor (○), the hydrolytic product (●) and $M_9GN_2$ (□, i.e., the remodeled product). FIG. 6 shows that the highest yield of the remodeled product was achieved at 20% acetone.

EXAMPLE 7
Remodeling of Glycopeptide Sugar Chain

A glycopeptide having a biantennary complex sugar chain was prepared by digesting bovine fibrinogen with a mixture of chymotrypsin and trypsin. This glycopeptide was purified by HPLC and its N-terminus was modified with a naphthylacetyl group.

Figure 7A:
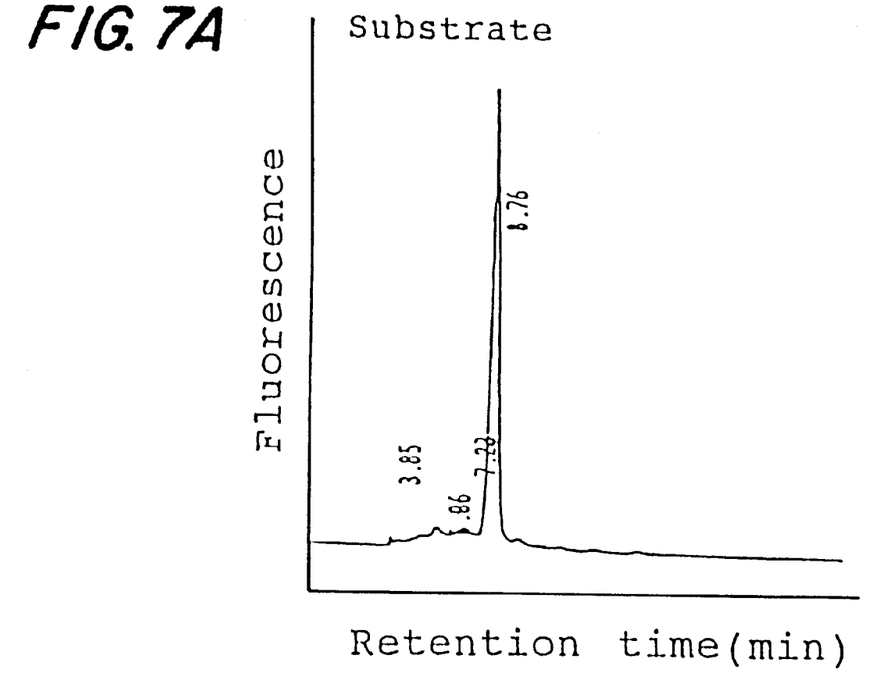
FIG. 7 shows the results of HPLC analysis on the glycopeptide before and after the digestion with Endo-M.
Figure 7B:
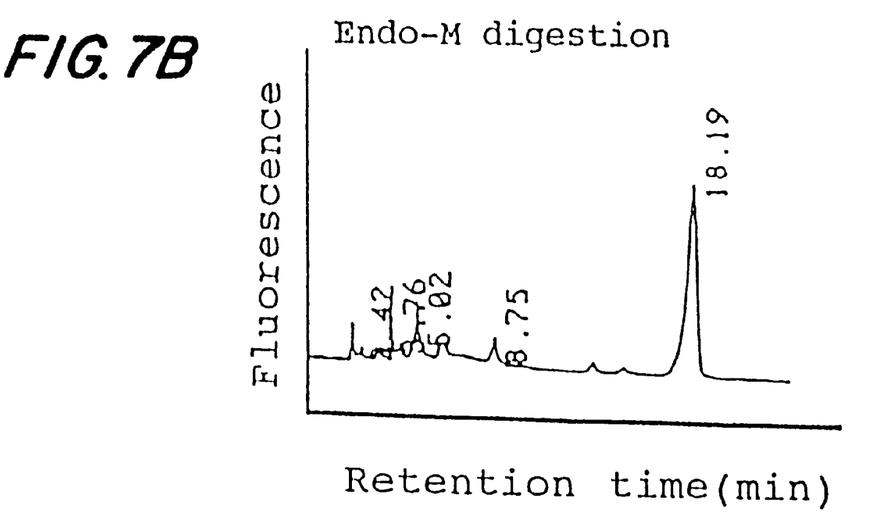
Figure 8:
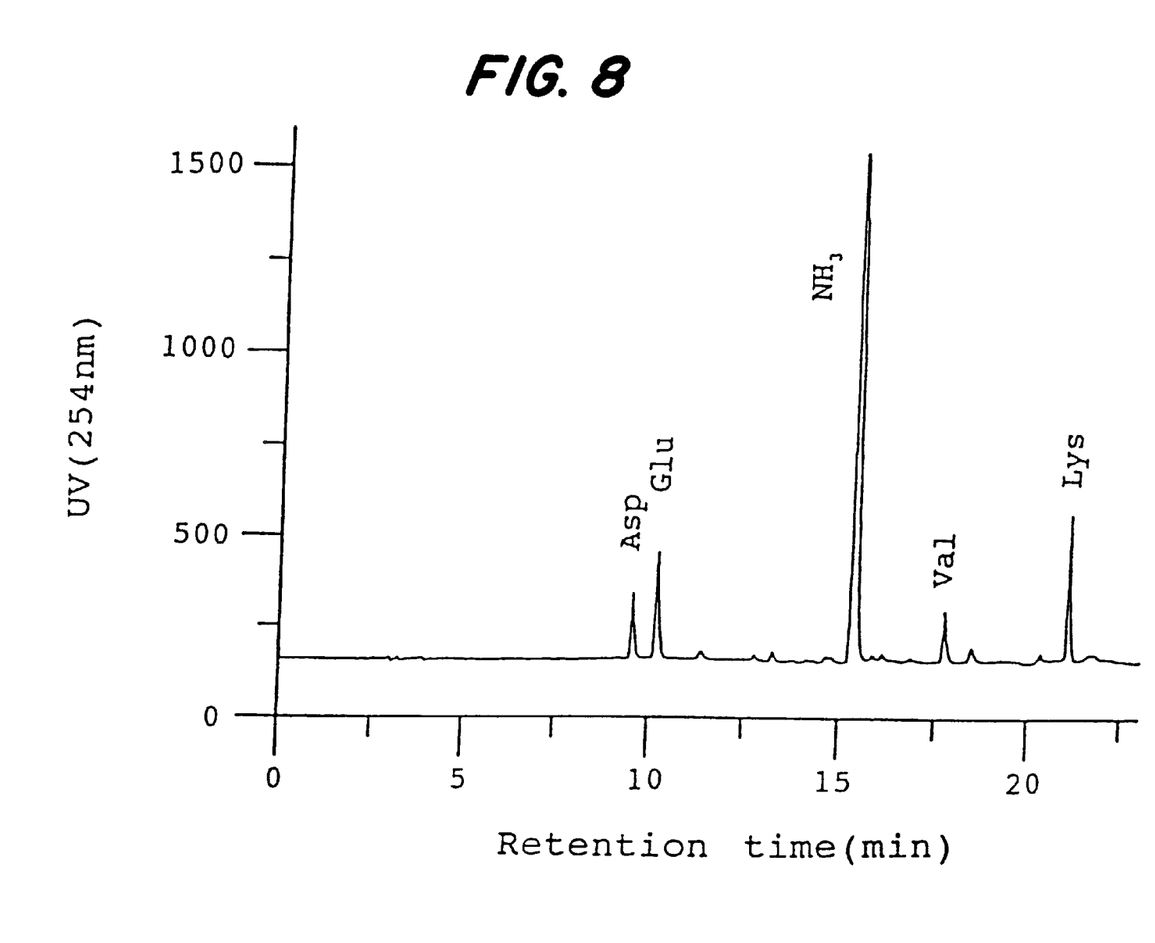
FIG. 8 shows the results of the analysis on the amino acid composition of the GlcNAc-pentapeptide.

Next, Endo-M from *Mucor hiemalis* [This strain was deposited on May 18, 1988 at National Institute of Bioscience and Human-Technology Agency of Industrial Science and Technology (1–3, Higashi 1 chome Tsukubashi Ibaraki-ken 305, JAPAN), in accordance with the Budapest Treaty under the accession number FERM BP-4991] was purified by a method described in *Agricultural and Biological Chemistry*, 54, 97–106 (1990). By using the enzyme, the above-mentioned glycopeptide was drastically digested. 1.3 ml of a 0.1M ammonium acetate buffer (pH 6.0) solution containing 1.25 mmol of the glycopeptide and 1.77 mU Endo-M was incubated at 37° C. overnight. The glycopeptide was analyzed by HPLC before and after the digestion with Endo-M. FIG. 7 shows the results. Namely, FIG. 7 shows the HPLC of the glycopeptide before the digestion with Endo-M (upper) and that of the digested glycopeptide (lower), wherein the ordinate refers to the fluorescence intensity, while the abscissa refers to the retention time (minutes). The HPLC was performed by an reverse phase (RP)-$C_8$ column (4.6×250 mm), a 50 mM ammonium acetate solution as the eluent A and a 50 mM ammonium acetate solution containing 50% acetonitrile as the eluent B. The elution was performed by using the solution B at a ratio of 45% at room temperature and at a flow rate of 1 ml/min. The glycopeptide was detected with a fluorometric detector with an excitation wavelength of 320 nm and a fluorescence wavelength of 380 nm. FIG. 7 shows that the glycopeptide had been almost completely digested and the biantennary complex sugar chain had been eliminated therefrom. This glycopeptide (GlcNAc-pentapeptide) from which the sugar chain had been eliminated was purified by HPLC and the amino acid composition thereof was analyzed. FIG. 8 shows the results. Namely, FIG. 8 shows the results of the analysis on the amino acid composition of the GlcNAc-pentapeptide wherein the ordinate refers to the ultraviolet absorption at 254 nm, while the abscissa refers to the retention time (minutes). As FIG. 8 shows, the GlcNAc-pentapeptide has an amino acid composition of Asp:Glu:Val:Lys 1:2:1:1. Based on the amino acid sequence of the fibrinogen which has been already reported, it has been found out that this glycopeptide has the following amino acid sequence:

Chemical formula 1

Gln-Val-Clu-Asn(CHO)-Lys (SEQ ID NO: 1)

(wherein CHO represent a sugar residue which is combined a amide group in Asn)

Figure 9A:
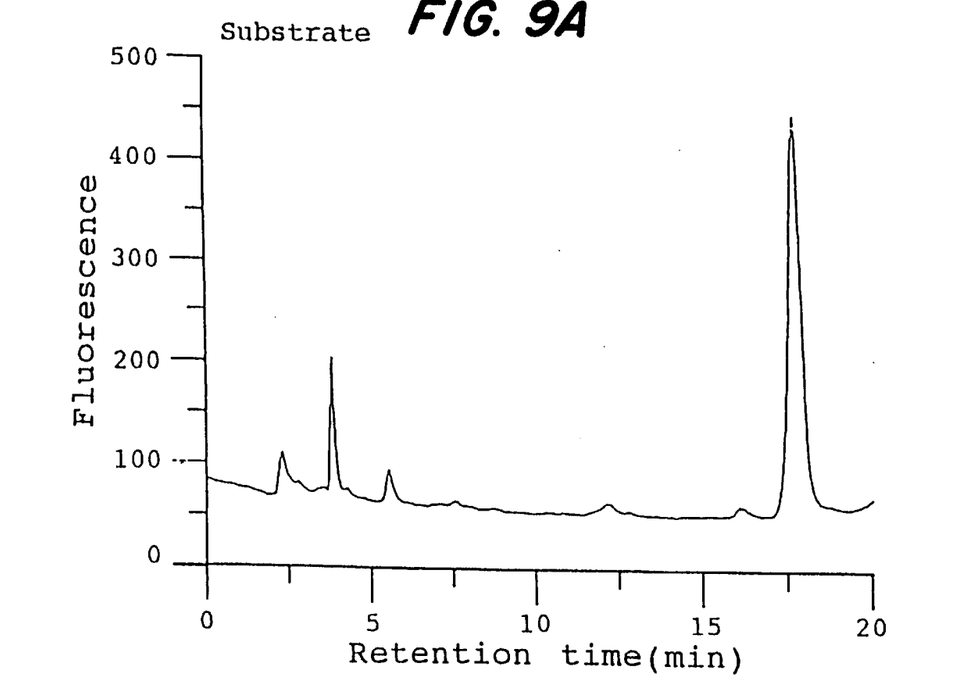
FIG. 9 shows the results of the HPLC analysis on the glycopeptide before and after the remodeling reaction.
Figure 9B:
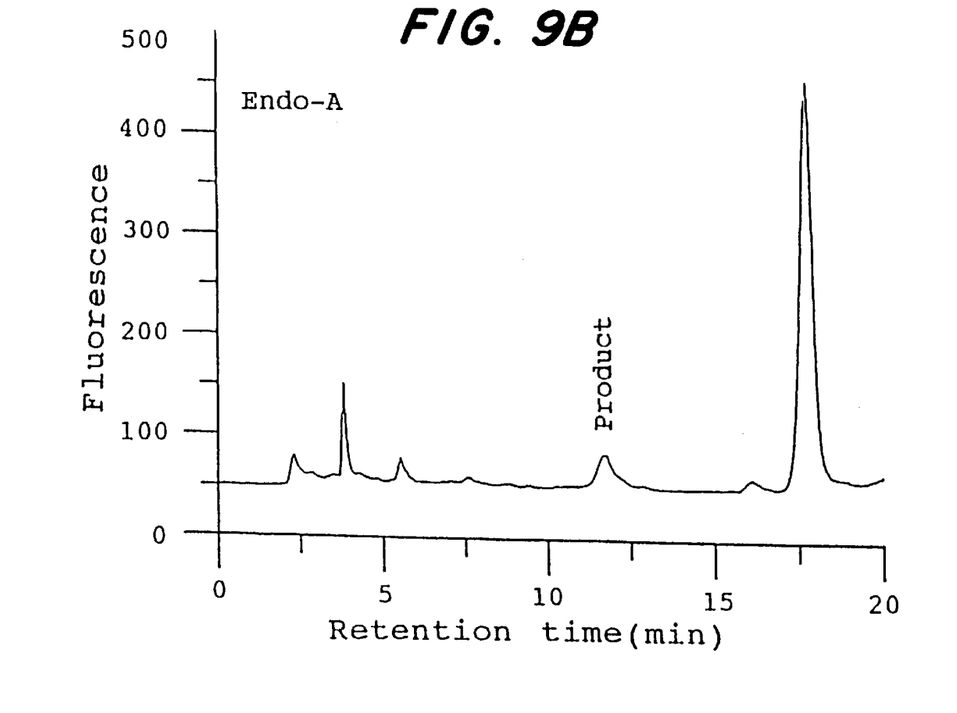

Next, 10 μl of a 50 mM ammonium acetate buffer solution (pH 6.0) containing 14 nmol GlcNAc-pentapeptide as the acceptor, 3 nmol $M_9GN_2$Asn as the donor, 3 mU Endo-A and 35% acetone was incubated at 37° C. for 15 minutes. Then the reaction mixture was subjected to HPLC analysis under the same conditions as those employed in the case of FIG. 7. FIG. 9 shows the results. Namely, FIG. 9 shows the HPLC of the glycopeptide before the remodeling (upper) and that of the remodeled glycopeptide (lower), wherein the ordinate refers to the fluorescence intensity, while the abscissa refers to the retention time (minutes). As FIG. 9 shows, a peak seemingly assignable to the remodeled product can be identified. The peak size of the chromatogram indicates that the yield of the remodeled product, i.e., GlcNAc-pentapeptide is about

EXAMPLE 8
Examination of Sugar Chain Transfer Reaction with Endo-A in Reaction Mixtures Containing Dioxane at Various Concentrations To a 25 mM acetate buffer (pH 6.0) were added 4 mU Endo-A and 100 mM GlcNAc and preincubated at 37° C. for 10 minutes. Then dioxane was added thereto in such a manner as to give reaction mixtures containing 0, 10, 20, 30, 40 and 50% dioxane. After adding 4 nmol of $M_6GN_2$Asn as the sugar chain donor, each reaction mixture (total volume: 40 μl) was incubated at 37° C. for 10 minutes to thereby perform the sugar chain transfer reaction. After terminating the reaction by heating to 100° C. for 3 minutes, the reaction mixture was labeled with 2-aminopyridine and analyzed by HPLC. Table 4 shows the results. As Table 4 shows that the transfer reaction almost completely prevailed over the hydrolysis at a dioxane concentration of 30% or above.

The labeling with 2-aminopyridine was performed by the method described in Japanese Patent Publication No. 65108/

1993. Then the $M_6GN_2$ thus labeled (hereinafter referred to simply as $M_6GN_2$-PA) and the $M_6GN$ thus labeled (hereinafter referred to simply as $M_6GN$-PA) were fractioned and determined. The yields (%) of the remodeled sugar chain listed in Table 4 were determined in accordance with the following Numerical formula 1.

$$\text{Yield of remodeled sugar chain} = \frac{(M_6GN_2 - PA \text{ formed})}{(M_6GN - PA \text{ formed} + M_6GN_2 - PA \text{ formed})} \times 100 \quad \text{Numerical formula 1}$$

TABLE 4

| dioxane concentrations (%) | Yields of the remodeled sugar chain (%) |
| --- | --- |
| 0 | 60 |
| 10 | 90 |
| 20 | 94 |
| 30 | 100 |
| 50 | 100 |

EXAMPLE 9

Change in Sugar Chain Transfer Reaction Product with the Passage of Time

Three vials, in each of which 4 mU Endo-A and 100 mM GlcNAc had been preincubated in a 25 mM acetate buffer (pH 6.0) at 37 ° C., were prepared. After 10 minutes, dioxane was added thereto to give final concentrations of 0, 20 and 30%. Next, $M_6GN_2$Asn serving as the sugar chain donor was added in 6 μg and the reaction was performed at 37° C. After 10, 30, 60, 90, 180 and 300 minutes, the reaction mixtures were sampled, heated at 100° C. for 3 minutes and then labeled with 2-aminopyridine. The $M_6GN_2$-PA thus formed was determined by HPLC. FIG. 4 shows the results. In FIG. 4, the ordinate refers to the yield (%) of $M_6GN_2$-PA based on the sugar chain donor (i.e., the yield of the remodeled sugar chain), while the abscissa refers to time (minutes).

As FIG. 4 shows, the yield of the remodeled product $M_6GN_2$ based on the sugar chain donor ($M_6GN_2$Asn) did not exceed 60% at a dioxane concentration of 20 or 0%. In the presence of 30% dioxane, the yield of $M_6GN_2$ amounted to 100% after 60 minutes. It was also found out that the transferred product would not be hydrolyzed even when the reaction was continued for additional 240 minutes.

EXAMPLE 10

Examination of the Acceptor Concentration in Sugar Chain Transfer Reaction with Endo-A in the Presence of 30% Dioxane By using 4 nmol $M_6GN_2$Asn as the sugar chain donor, 4 mU Endo-A was preincubated at 37° C. for 10 minutes in a 25 mM acetate buffer (pH 6.0) containing 30% dioxane in reaction vials with various concentrations of GlcNAc employed as the acceptor (0, 10, 50, 100, 200, 300 and 500 mM), thus performing a sugar chain transfer reaction. After terminating the reaction by heating at 100° C. for 3 minutes, the $M_6GN_2$ thus formed was labeled with 2-aminopyridine and analyzed by HPLC. FIG. 5 shows the results. In FIG. 5, the ordinate refers to the yield (%) of $M_6GN_2$-PA based on the sugar chain donor (i.e., the yield of the remodeled sugar chain), while the abscissa refers to the GlcNAc concentration (M). As FIG. 5 shows, the transfer reaction almost completely prevailed over the hydrolysis at a GlcNAc concentration of 100 mM or above.

Effects of the Invention

The present invention provides a process for producing a remodeled sugar chain without forming any by-products. The process of the present invention is useful particularly in the production of a substance containing a remodeled sugar chain which is a physiologically active substance that plays an important role in vivo.

We claim:

1. A process for producing a carbohydrate or glycoconjugate of the formula A-C by a transfer reaction as shown in formula (I), comprising reacting A-B and C as shown in formula (I) in an aqueous medium containing about 10%–50% by volume of a water-soluble ketone and/or dioxane in the presence of a endo-β-N-acetylglucosaminidase selected from the group consisting of Endo-A and Endo-M, $$A-B+C \rightarrow A-C+B \qquad (I)$$

wherein A represents a GlcNAc-containing compound, B represents a carbohydrate or a glycoconjugate and C represents a carbohydrate or a glycoconjugate, to form the carbohydrate or glycoconjugate of the formula A-C.

2. The process as claimed in claim 1, wherein said water-soluble ketone is selected from the group consisting of acetone, methyl ethyl ketone and dimethyl ketone.

* * * * *